US011147701B2

(12) United States Patent
Jones et al.

(10) Patent No.: US 11,147,701 B2
(45) Date of Patent: Oct. 19, 2021

(54) WEARABLE FOOT GARMENT

(71) Applicant: Apolla Performance Wear LLC, Fort Worth, TX (US)

(72) Inventors: Kaycee Jones, Atlanta, GA (US); Aiesha Ashby, Fort Worth, TX (US)

(73) Assignee: APOLLA PERFORMANCE WEAR LLC, Fort Worth, TX (US)

( * ) Notice: Subject to any disclaimer, the term of this patent is extended or adjusted under 35 U.S.C. 154(b) by 464 days.

(21) Appl. No.: 16/133,419

(22) Filed: Sep. 17, 2018

(65) Prior Publication Data
US 2019/0083290 A1 Mar. 21, 2019

Related U.S. Application Data

(63) Continuation of application No. 15/040,765, filed on Feb. 10, 2016, now Pat. No. 10,076,436, which is a
(Continued)

(51) Int. Cl.
A61F 5/01 (2006.01)
A43B 7/14 (2006.01)
(52) U.S. Cl.
CPC .......... A61F 5/0111 (2013.01); A43B 7/1445 (2013.01); A43B 7/1495 (2013.01)
(58) Field of Classification Search
CPC ...... A61F 13/08; A61F 13/00; A61F 13/0273; A61F 5/40; A61F 13/061; A61F 13/10;
(Continued)

(56) References Cited

U.S. PATENT DOCUMENTS 1,693,174 A 11/1928 Capezio
1,704,281 A 3/1929 Capezio
(Continued)

FOREIGN PATENT DOCUMENTS

WO 2012067645 5/2012
WO 2013063554 5/2013
(Continued)

OTHER PUBLICATIONS

Co-pending Design U.S. Appl. No. 29/663,623, filed Sep. 17, 2018.

Primary Examiner — Ophelia A Hawthorne
(74) Attorney, Agent, or Firm — Meunier Carlin & Curfman LLC

(57) ABSTRACT

Various implementations include a wearable foot garment that includes a forefoot portion, a midfoot portion, and an ankle portion. The midfoot portion includes two high compression zones and a reduced compression zone between the high compression zones. The first high compression zone is configured for providing compression in a radially inward direction toward the wearer's foot adjacent a proximal end of the wearer's plantar aponeurosis. The second high compression zone is configured for providing compression in a radially inward direction toward the wearer's foot adjacent distal ends of metatarsals of the wearer. The compressive strength in the high compression zones is greater than the compressive strength in the reduced compression zone. In some implementations, the ankle portion and midfoot portion define a heel opening, and the forefoot portion includes a plantar surface area on which an adhesive film is disposed for increasing the friction contact of the forefoot portion.

14 Claims, 14 Drawing Sheets

Related U.S. Application Data continuation-in-part of application No. 14/965,804, filed on Dec. 10, 2015, now abandoned.

(60) Provisional application No. 62/090,145, filed on Dec. 10, 2014, provisional application No. 62/101,202, filed on Jan. 8, 2015, provisional application No. 62/201,938, filed on Aug. 6, 2015.

(58) Field of Classification Search
CPC .......... A61F 5/0109; A61F 13/107; A61F 2013/00102; A61F 2013/00119; A61F 13/065; A61F 13/066; A61F 5/0111; A61F 5/0195; D04B 1/265; D04B 11/28; D04B 1/06; A41B 11/00; A43B 7/142

See application file for complete search history.

(56) References Cited

U.S. PATENT DOCUMENTS

| | | | |
|---|---|---|---|
| 1,813,561 A | 7/1931 | Capezio | |
| 1,819,766 A | 8/1931 | Capezio | |
| 1,872,641 A | 8/1932 | Capezio | |
| 1,891,022 A | 12/1932 | Capezio | |
| 2,237,652 A | 4/1941 | Capezio | |
| 3,013,564 A | 12/1961 | Levey | |
| 4,522,044 A | 6/1985 | Lineberry et al. | |
| 5,185,000 A | 2/1993 | Brandt et al. | |
| 5,617,745 A | 4/1997 | Della Corte et al. | |
| 5,704,137 A | 1/1998 | Dean et al. | |
| D403,149 S | 12/1998 | Fincher | |
| 6,158,253 A | 12/2000 | Svoboda et al. | |
| 6,393,620 B2 | 5/2002 | Hatch et al. | |
| 6,708,348 B1 | 3/2004 | Romay | |
| 6,805,681 B2 | 10/2004 | Yokoyama | |
| D499,807 S | 12/2004 | Stauffer | |
| 6,936,021 B1 | 8/2005 | Smith | |
| D513,116 S | 12/2005 | Gaither | |
| 7,069,600 B1 | 7/2006 | Romay | |
| 7,346,935 B1 | 3/2008 | Patterson | |
| D590,590 S | 4/2009 | Bonzagni et al. | |
| D613,491 S | 4/2010 | Hollingsworth et al. | |
| 7,950,071 B2 | 5/2011 | Jeong | |
| RE43,213 E | 2/2012 | Romay | |
| D657,122 S | 4/2012 | Gaither | |
| D657,123 S | 4/2012 | Gaither | |
| 8,272,073 B2 | 9/2012 | Arensdorf et al. | |
| D678,538 S | 3/2013 | Huthmaker | |
| D679,822 S | 4/2013 | Huthmaker | |
| 8,495,765 B2 | 7/2013 | Araki et al. | |
| 8,505,120 B2 | 8/2013 | Lambertz | |
| D707,035 S | 6/2014 | Patterson | |
| D710,593 S | 8/2014 | Goodman et al. | |
| 8,881,428 B2 | 11/2014 | Mackey et al. | |
| D722,382 S | 2/2015 | Lee et al. | |
| 8,973,411 B2 | 3/2015 | Gaither | |
| D734,938 S | 7/2015 | Patterson | |
| 9,204,986 B2 | 12/2015 | Higgins | |
| 9,226,842 B2 | 1/2016 | Sellitto | |
| D751,805 S | 3/2016 | Patterson | |
| D752,851 S | 4/2016 | Patterson | |
| D752,852 S | 4/2016 | Patterson | |
| 9,414,639 B2 | 8/2016 | Heathcote | |
| 9,439,828 B2 | 9/2016 | Mayer et al. | |
| D774,296 S | 12/2016 | Patterson | |
| D775,812 S | 1/2017 | Patterson | |
| D775,813 S | 1/2017 | Patterson | |
| D778,041 S | 2/2017 | Patterson | |
| 9,603,748 B2 | 3/2017 | Valois et al. | |
| D786,548 S | 5/2017 | Patterson | |
| 9,713,349 B2 | 7/2017 | Campbell | |
| 9,750,643 B2 | 9/2017 | Convert et al. | |
| 9,757,302 B2 | 9/2017 | Mayer | |
| D799,812 S | 10/2017 | Bennett | |
| 9,777,413 B2 | 10/2017 | Messier | |
| D802,292 S | 11/2017 | Patterson | |
| D803,543 S | 11/2017 | Scott et al. | |
| D804,162 S | 12/2017 | Patterson | |
| 9,850,601 B2 | 12/2017 | Shen et al. | |
| D821,068 S | 6/2018 | Coleman | |
| D837,988 S | 1/2019 | Khubani et al. | |
| D844,157 S | 3/2019 | Lind et al. | |
| D859,670 S | 9/2019 | Rokitta | |
| 2003/0145491 A1 | 8/2003 | Udugama | |
| 2005/0091725 A1 | 5/2005 | Alley | |
| 2005/0091729 A1 | 5/2005 | Alley | |
| 2006/0195972 A1 | 9/2006 | Alley | |
| 2007/0113593 A1 | 5/2007 | Jeong | |
| 2008/0127520 A1* | 6/2008 | Luedecke | A43B 7/18 36/102 |
| 2008/0156044 A1 | 7/2008 | Patterson | |
| 2009/0223254 A1 | 9/2009 | Ishida | |
| 2012/0017354 A1 | 1/2012 | Vadnais | |
| 2012/0090077 A1 | 4/2012 | Brown | |
| 2012/0102625 A1 | 5/2012 | Klein | |
| 2012/0284902 A1 | 11/2012 | Matsuo et al. | |
| 2013/0145521 A1 | 6/2013 | Spicuzza et al. | |
| 2013/0233629 A1 | 10/2013 | Gaither | |
| 2014/0033567 A1 | 2/2014 | Heathcote et al. | |
| 2014/0058311 A1 | 2/2014 | Higgins | |
| 2014/0338090 A1 | 11/2014 | Perkins | |
| 2014/0352170 A1 | 12/2014 | Heathcote | |
| 2015/0181979 A1 | 7/2015 | Gaither | |
| 2015/0351492 A1 | 12/2015 | Dombrow et al. | |
| 2015/0366735 A1 | 12/2015 | Barker | |
| 2016/0081840 A1 | 3/2016 | Higgins | |
| 2016/0120248 A1 | 5/2016 | Oliver | |
| 2016/0219973 A1 | 8/2016 | Cheney et al. | |
| 2016/0295962 A1 | 10/2016 | Craig et al. | |
| 2016/0331633 A1 | 11/2016 | Mayer et al. | |
| 2016/0340813 A1 | 11/2016 | Amis et al. | |
| 2016/0360797 A1 | 12/2016 | Baravarian | |
| 2017/0056231 A1 | 3/2017 | Hara et al. | |
| 2017/0100300 A1 | 4/2017 | Rapp et al. | |
| 2017/0354543 A1 | 12/2017 | Mazourik et al. | |
| 2017/0367868 A1 | 12/2017 | Ducharme | |
| 2018/0036160 A1 | 2/2018 | Ellicott | |
| 2018/0042339 A1 | 2/2018 | Barnes et al. | |
| 2018/0051401 A1 | 2/2018 | Giorgini | |

FOREIGN PATENT DOCUMENTS

| | | |
|---|---|---|
| WO | 2017173441 | 10/2017 |
| WO | 2018015775 | 1/2018 |
| WO | 2018025238 | 2/2018 |

* cited by examiner

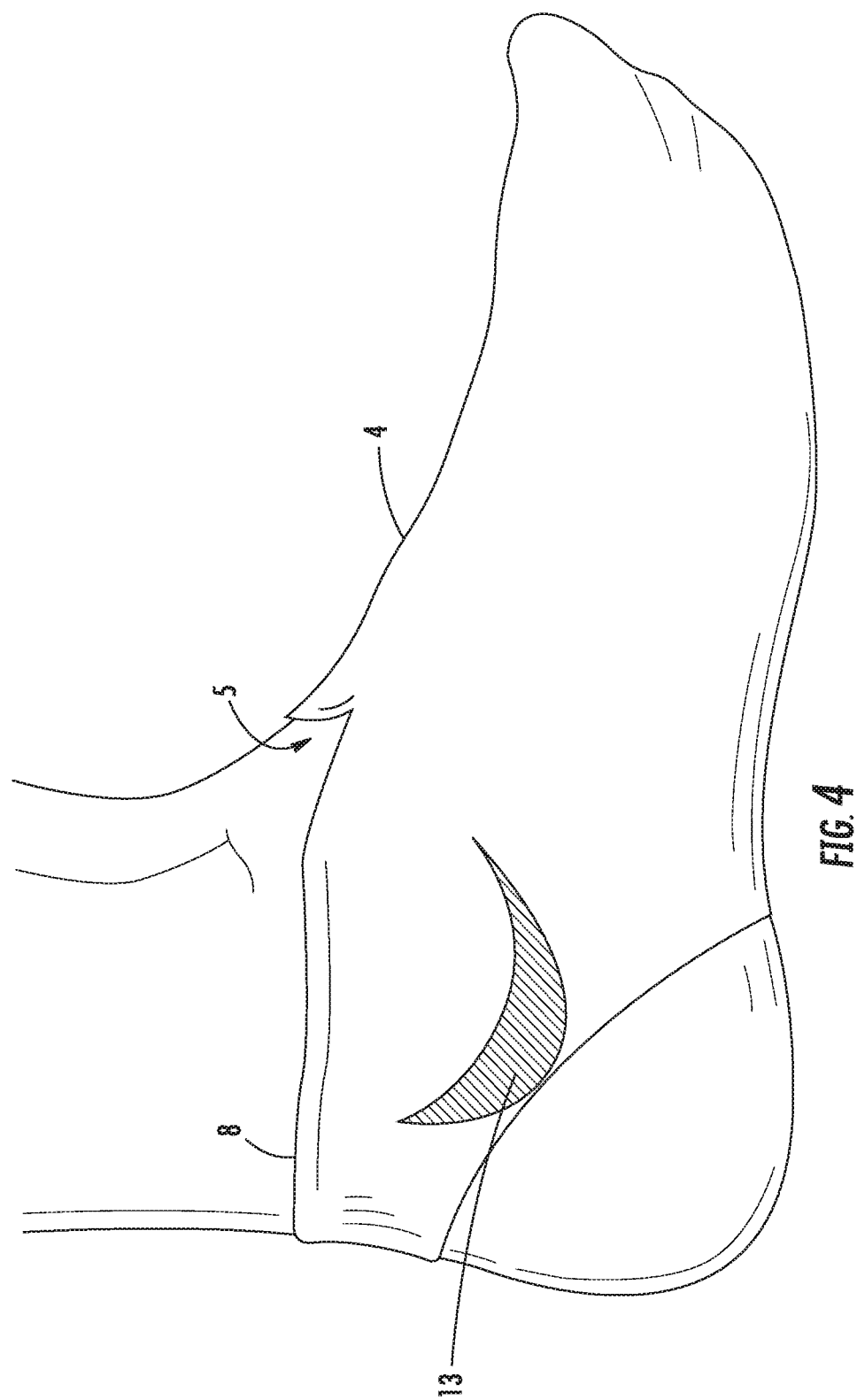

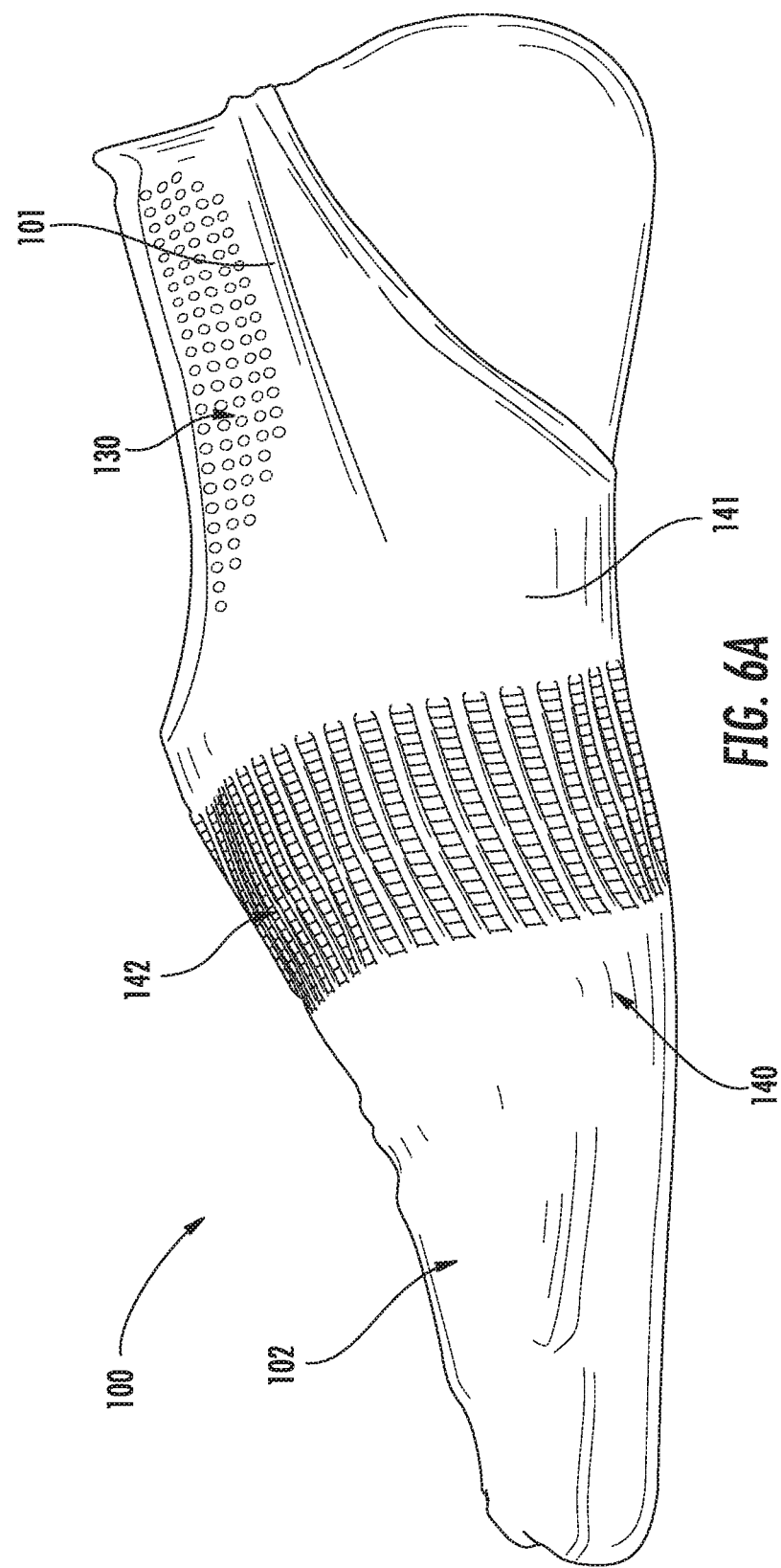

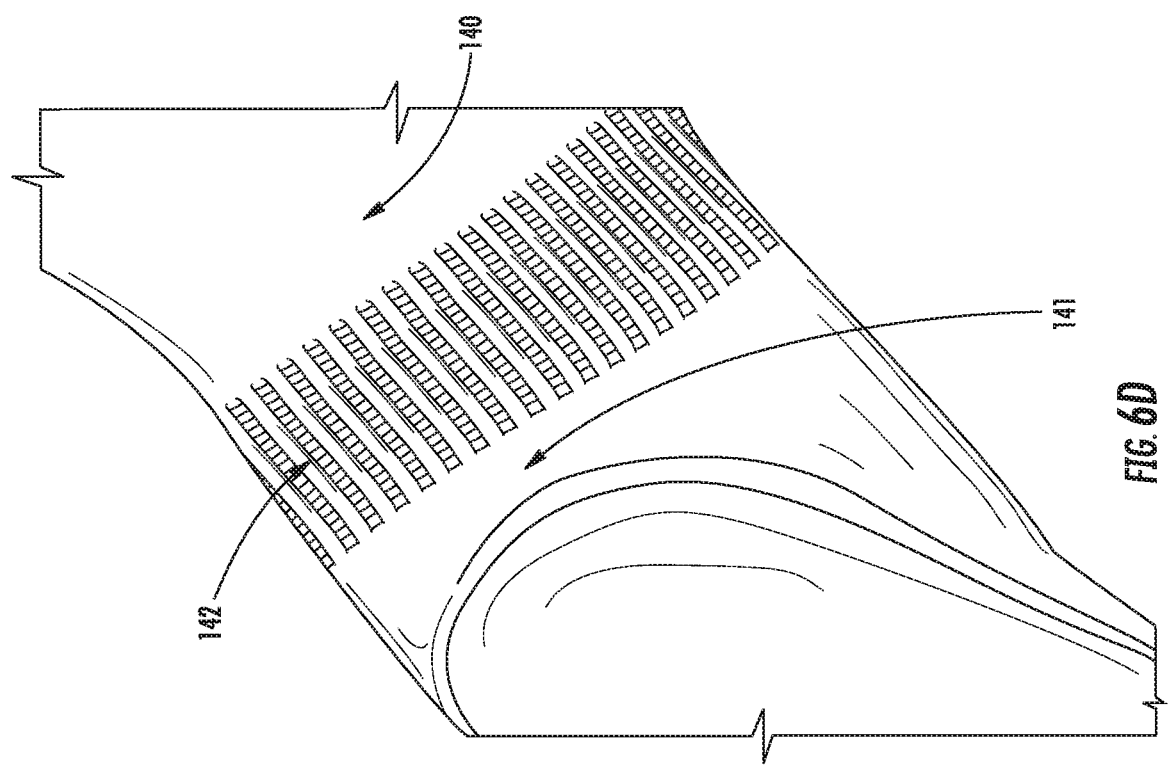

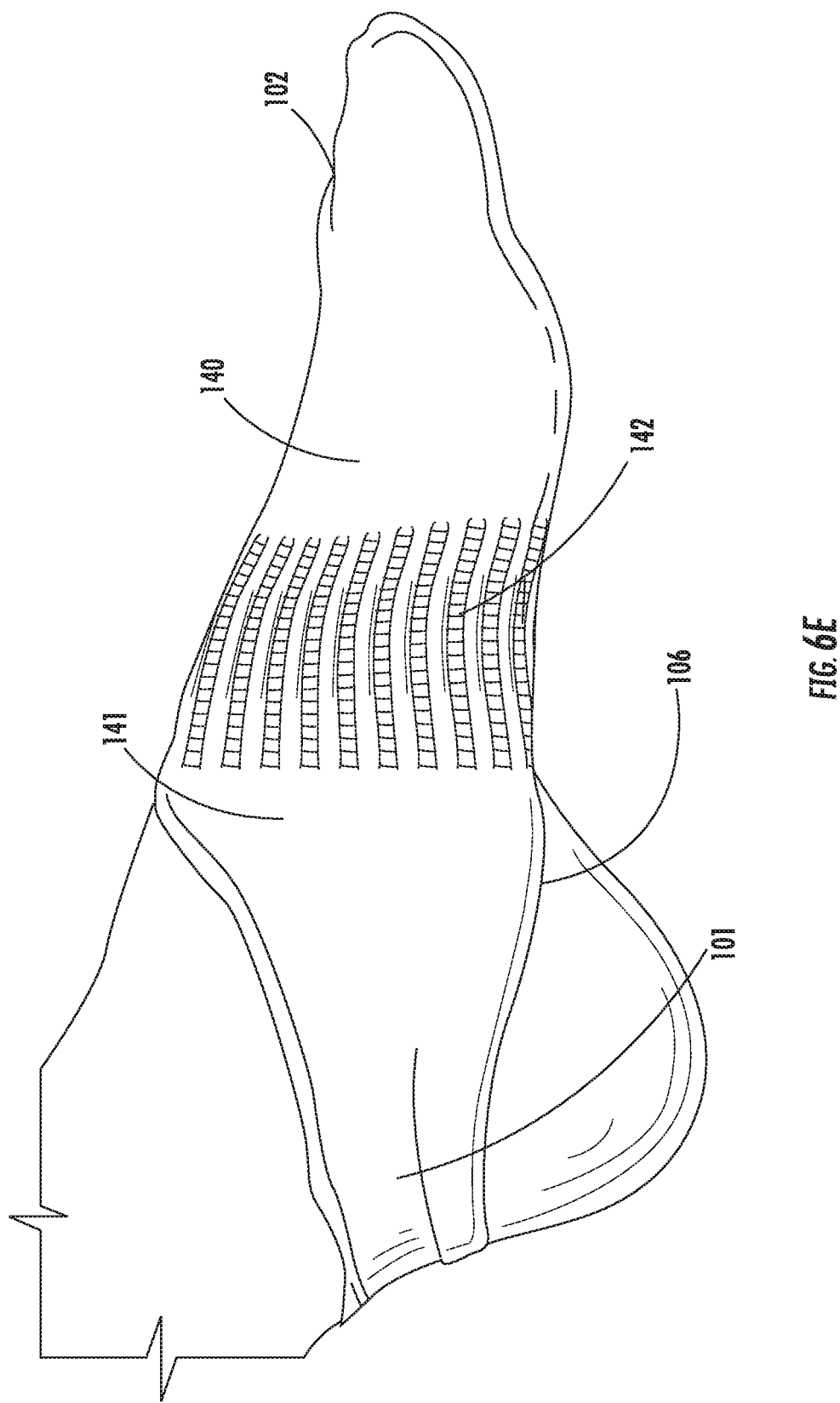

WEARABLE FOOT GARMENT

CROSS REFERENCE TO RELATED APPLICATIONS

This application is a continuation of U.S. patent application Ser. No. 15/040,765, filed Feb. 10, 2016 and entitled "Wearable Foot Garment" (and which issued as U.S. Pat. No. 10,076,436 on Sep. 18, 2018), which is a continuation in part application of U.S. patent application Ser. No. 14/965,804, filed Dec. 10, 2015 and entitled "Wearable Foot Garment," which claims priority to U.S. Provisional Patent Application No. 62/090,145, entitled "An Athletic Sock," filed Dec. 10, 2014, U.S. Provisional Patent Application No. 62/101,202, entitled "An Athletic Sock," filed Jan. 8, 2015, and U.S. Provisional Patent Application No. 62/201,938, entitled "An Athletic Sock," filed Aug. 6, 2015, the contents of which are herein incorporated by reference in their entireties.

BACKROUND

The plantar fascia is connective tissue that runs between the distal ends of the metatarsal bones of the foot to the protuberance of the calcaneus bone. The planta fascia may be become inflamed from overuse or lack of arch support. Current arch support mechanisms include orthotics, which are worn within a shoe between the sole of the shoe and a plantar surface of the wearer's foot. However, wearers performing studio-type exercises, such as dance, aerobics, yoga, Pilates, Barre, etc., do not typically wear shoes while exercising.

Thus, there is a need in the art for a wearable foot garment that supports the plantar fascia to help prevent or recover from injury to the plantar fascia and that can be worn during exercise.

BRIEF SUMMARY

Various implementations include a wearable foot garment that includes a forefoot portion, a midfoot portion, and an ankle portion. The forefoot portion has a plantar area and a dorsal area. The plantar and dorsal areas may be coupled together to define a pocket configured for receiving the wearer's toes. The midfoot portion includes a first high compression zone, a second high compression zone, and a reduced compression zone disposed between the first and second high compression zones. The first high compression zone and the second high compression zone extend at least along a plantar area of the midfoot portion and at least partially around a circumference of the midfoot portion. The first high compression zone is configured for providing compression in a radially inward direction toward the wearer's foot adjacent a proximal end of the wearer's plantar aponeurosis. The second high compression zone is configured for providing compression in a radially inward direction toward the wearer's foot adjacent distal ends of metatarsals of the wearer. The reduced compression zone extends at least along the plantar area of the midfoot portion and at least partially around the circumference of the midfoot portion, and it is disposed between the first and second high compression zones. A first compressive strength in the first high compression zone and a second compressive strength associated in the second compression zone are greater than a third compressive strength in the reduced compression zone.

In some implementations, the ankle portion comprises an ankle band that has a first edge that defines a leg opening and a second edge that defines a heel opening with a proximal edge of the midfoot portion. The leg opening is configured for receiving a leg of the wearer, and the heel opening is configured for receiving at least a portion of a heel of the wearer.

The ankle band has a compressive strength that is substantially the same as the compressive strength of the first high compression zone, according to some implementations. In addition, the ankle portion may include a first ankle band and a second ankle band. Each of the first ankle band and the second ankle band includes a proximal end knit together with the midfoot portion adjacent the first high compression zone and a distal end.

In some implementations, the distal ends of the ankle bands may be coupled together along a seam and/or a distal end of the forefoot portion may include a seam. The proximal ends of the ankle bands, the midfoot portion, and the forefoot portion may be knit together seamlessly.

In addition, the dorsal area of the forefoot portion may have substantially the same compressive strength as the first high compression zone, and the plantar area of the forefoot portion may have less compressive strength than the first high compression zone. Furthermore, in some implementations, the first high compressive zone, the second high compressive zone, and/or the reduced compression zone extend around the circumference of the midfoot portion 360°.

In some implementations, the plantar area of the forefoot portion includes a shock absorbing yarn.

In some implementations, the plantar area of the forefoot portion includes an adhesive film disposed on an external surface of the plantar area. The adhesive film may have a co-efficient of friction that is higher than an external surface of the midfoot portion. At least a portion of the adhesive film may be configured for engaging a ground surface when the wearable foot garment is worn by the wearer. In addition, in some implementations, the plantar area of the forefoot portion further comprises a layer of paint, and a portion of the adhesive film is disposed between the external surface of the plantar area and the layer of paint.

In other implementations, the wearable foot garment further includes a lower leg portion extending axially from the ankle portion and configured for wrapping circumferentially around at least a lower leg of the wearer. A compressive strength of the lower leg portion decreases axially from the ankle portion toward a leg opening defined by the lower leg portion. And, in some implementations, a fourth compressive strength in the ankle portion is substantially the same as the second compressive strength in the second high compression zone.

BRIEF DESCRIPTION OF THE DRAWINGS

Various implementations of the wearable foot garment are explained in even greater detail in the following exemplary drawings. The drawings are merely exemplary to illustrate the structure of the garment and certain features that may be used singularly or in combination with other features. The invention should not be limited to the implementations shown.

FIG. 4 illustrates an outer side schematic view of a sock according to another implementation.

FIG. 6A illustrates an outer side view of a sock according to another implementation.

FIG. 6D illustrates a partial top view of the sock of FIG. 6A.

FIG. 6E illustrates a full view of the inner side of the sock of FIG. 6A.

DETAILED DESCRIPTION

Figure 1:
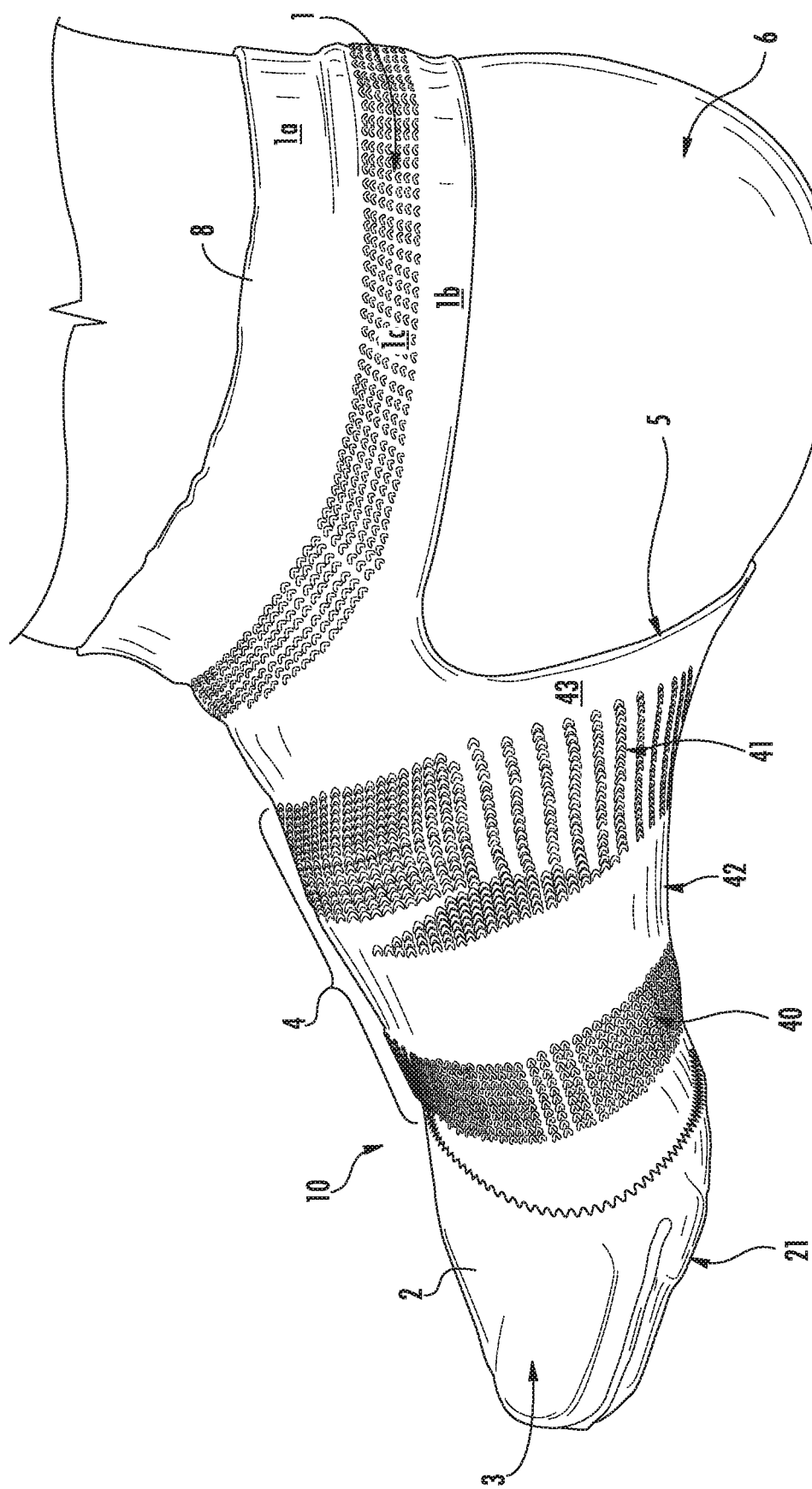
FIG. 1 illustrates a side view of a sock according to one implementation.

Various implementations include a wearable foot garment that incorporates sports science technology engineered for performance enhancement, preventative maintenance, plantar fascia and/or Achilles tendon support, and recovery. For example, the wearable foot garment may be a knit sock. The wearable foot garment may be particularly useful for dancers and other athletes. According to various implementations, the wearable foot garment may provide: shock absorption below the forefoot ball of the foot), ankle joint stabilization through compression, arch support using targeted compression, and/or Achilles tendon support using targeted compression. In addition, in certain implementations, the wearable foot garment may also provide traction on a plantar (or bottom) surface of the sock that is proper for a particular or for a variety of dance floor surfaces (e.g., marley, carpeted, wood, etc.). Some implementations may also (or alternatively) provide medical grade graduated compression along a wearer's lower leg for improved circulation and muscle recovery. The wearable foot garment may also be configured for providing a fashionable and aesthetically pleasing appearance for a dancer or other performer or athlete.

In various implementations, the wearable foot garment has one or more of the following features: seamless knitting, soft fabric and feel, high quality graduated compression technology in key areas on the foot and/or ankle for preventative maintenance and support, non-chafing, does not limit range of motion of the foot or ankle, fits various sizes of feet, feels like a second skin, provides shock absorption below forefoot but does not inhibit the wearer from feeling the floor, is aesthetically pleasing to the wearer, and provides a sufficient amount of traction for the wearer on various types of floor surfaces on which the wearer may be performing, or any combination thereof.

In particular, various implementations include a wearable foot garment that includes a forefoot portion, a midfoot portion, and an ankle portion. The midfoot portion, which is configured to fit adjacent a wearer's midfoot, includes two high compression zones and a reduced compression zone between the high compression zones. The first high compression zone is configured for providing compression in a radially inward direction toward the wearer's foot adjacent a proximal end of the wearer's plantar aponeurosis, which is part of the plantar fascia. The second high compression zone is configured for providing compression in a radially inward direction toward the wearer's foot adjacent distal ends of metatarsals of the wearer. The compressive strength in the high compression zones is greater than the compressive strength in the reduced compression zone. In some implementations, the ankle portion defines a leg opening, and the ankle portion and midfoot portion define a heel opening. In other implementations, the wearable foot garment further comprises a leg opening that extends from the ankle portion and is configured for providing graduated compression to at least a portion of the wearer's lower leg. In addition, in certain implementations, the forefoot portion includes a plantar surface area on which an adhesive film is disposed. Once the adhesive film is dried, the film is configured to increase the frictional contact of the plantar surface area of the forefoot portion with the floor.

Figure 3:
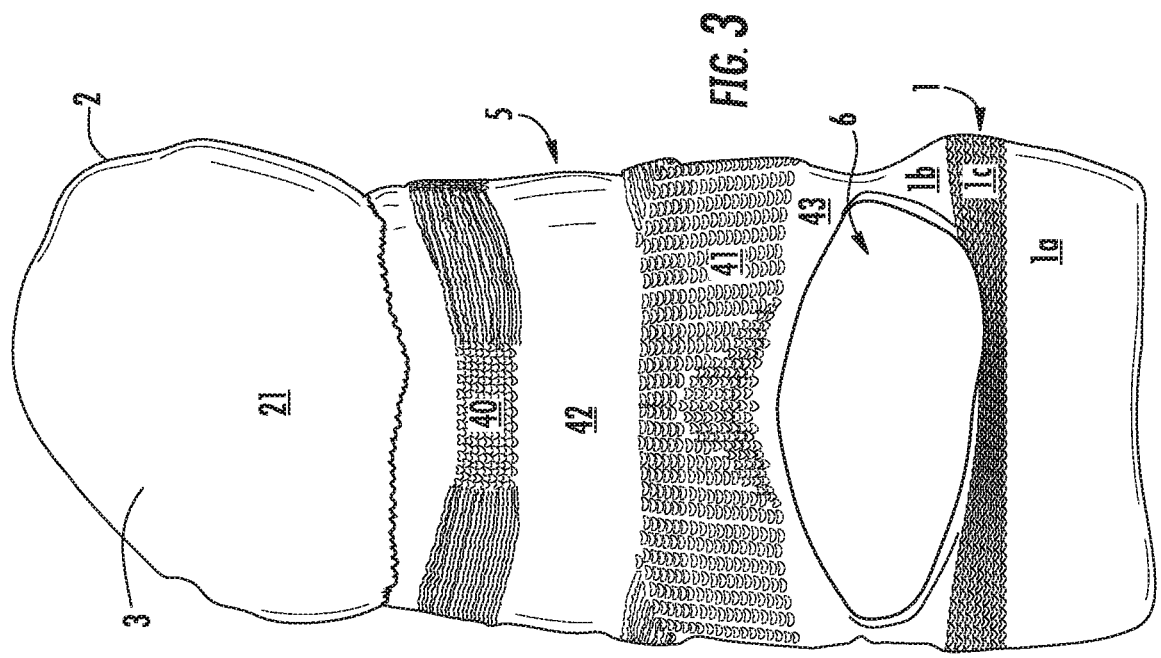
FIG. 3 illustrates a bottom view of the sock in FIG. 1.
Figure 2:
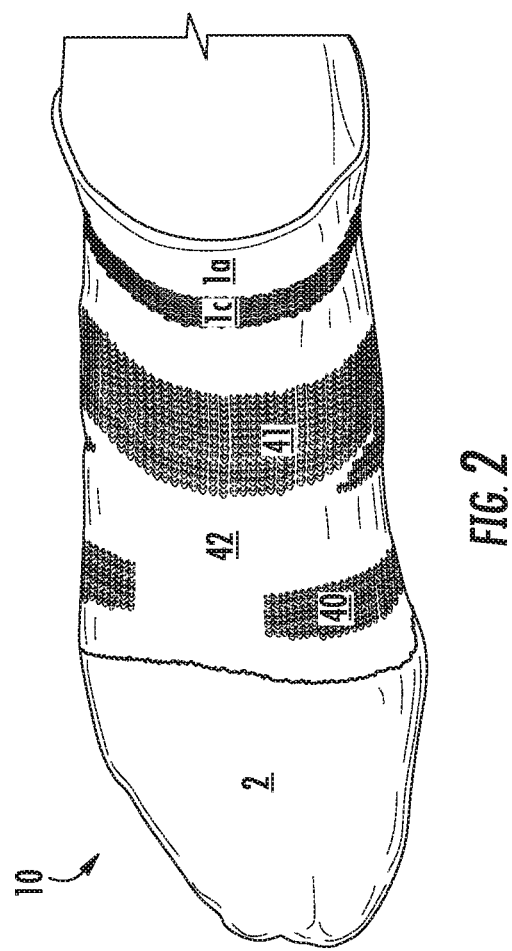
FIG. 2 illustrates a top view of the sock in FIG. 1.

One implementation of the sock 10 is shown in FIGS. 1 through 3. The sock 10 includes an ankle portion 1 and a foot portion 5. The ankle portion 1 includes an upper single welt band 1a that extends around the ankle of the wearer, a lower single welt band 1b that extends partially around the back and sides of the ankle of the wearer just above the heel, and an intermediate compression band 1c disposed between the bands 1a, 1b that provides a higher compressive strength than is provided by the upper and lower welt bands 1a, 1c. This compression band 1c provides support for the ankle and Achilles tendon. In other implementations, the upper and lower bands 1a, 1b may instead have another suitable knit pattern. In some embodiments, such as shown in FIG. 4, the sock 10 further includes a crescent shaped knit pattern 13 disposed just below the distal end of the fibula, or lateral malleolus, which is the bony protrusion on the outside of the ankle. This crescent shaped knit pattern 13 may be configured for supporting the ligaments that connect to the distal end of the fibula.

The foot portion 5 includes a midfoot portion 4 that is configured for extending around the midfoot of the wearer and a forefoot portion 2 that is configured for extending around the forefoot of the wearer. The midfoot portion 4 includes a single welt band 43 along a proximal edge thereof. Band 43 and band 1b define an opening 6 through which the wearer's heel may extend. Having the heel opening 6 provides traction for the wearer and a more "barefoot" feel to the wearer. Some styles of dancers, for example, are accustomed to dancing without shoes or socks. Thus, having the barefoot feel is more in line with what these dancers may expect and would feel comfortable wearing. As mentioned above, in other implementations, the band 43 may instead have another suitable knit pattern.

The midfoot portion 4 also includes a proximal high compression band 41, a distal high compression band 40, and an intermediate, reduced compression arch band 42 that is disposed between the proximal high compression band 41 and the distal high compression band 40. The proximal high compression band 41 is configured for extending around at least a portion of the circumference of the midfoot of the wearer such that the band 41 provides compression radially inwardly adjacent a proximal end of the plantar aponeurosis, which is coupled to the calcaneus, or heel, bone. The distal high compression band 40 is configured for extending around at least a portion of the circumference of the midfoot of the wearer such that the band 40 provides compression radially inwardly adjacent distal ends of the metatarsal bones. The high compression bands 40, 41 provide a higher compressive strength to the foot than the portions of the sock directly adjacent to them. According to some implementations, this compressive strength provided by the bands 40, 41 allows the sock to support the plantar fascia of the wearer at points where the plantar fascia may tear away from the heel bone or metatarsals in response to over use or pressure from the wearer. The compressive strength provided by the bands 40, 41 may be substantially the same or different.

The intermediate arch band 42 disposed between the high compression bands 40, 41 provides less compression than the bands 40, 41. For example, the ideal average compressive strength to be applied by the high compression bands 40, 41 may be at least about 24 mmHg (e.g., between about 24 mmHg and about 30 mmHg), and the ideal average compressive strength to be applied by the intermediate, reduced compression arch band 42 may be greater than 75% (e.g., greater than 75%, greater than 80%, greater than 85%, greater than 90%, or greater than 95%) of the average compressive strength applied by the high compression bands 40, 41. For example, the ideal average compressive strength of the high compression bands 40, 41 may be between about 24 mmHg and about 25 mmHg, and the ideal average compressive strength of the reduced compression band 42 may be between about 19 mmHg and about 20 mmHg. As another example, the ideal average compressive strength of high compression band 40 may be between about 25 and about 26 mmHg, the ideal average compressive strength of high compression band 41 may be between about 26 and 27 mmHg, and the ideal average compressive strength of the reduced compression band 42 may be between about 21 mmHg and about 23 mmHg.

Because the various bands 40, 41, 42 of sock 10 do not have an axial length greater than a minimum axial length required for known compression testing equipment and methods, the average compressive strength for each band 40, 41, 42 may be estimated by testing one or more samples of a knit tube that is formed using the same specifications as are used to form the respective band 40, 41, 42 and is knit to be at least the minimum axial length required for testing. The sample knit tube(s) may have a circumference of 23 mm and be tested using a modified BS 6612 test method on a CMD-100 Compression Measurement Test System.

Furthermore, in some implementations, one or both of the bands 40, 41 may extend around the full circumference of the wearer's foot, and in other implementations, one or both bands may stop short of extending around the full circumference. For example, as shown in FIG. 2, the distal high compression band 40 extends along a plantar surface and sides of the wearer's foot and partially along a portion of a dorsal (or upper) surface of the wearer's foot, but it does not extend fully around the wearer's foot like the proximal high compression band 41.

In some implementations, the distal high compression band 40 may be widened in an axial direction such that one edge of the band 40 extends to the proximal edge of the forefoot portion 2. In addition, the proximal high compression band 41 may be knitted or formed continuously with the ankle portion 1, such as is shown in FIGS. 6A-8. And, in some implementations, the high compression zones and/or the ankle portion may have similar stitch patterns, such as is shown in FIGS. 6A through 8.

Figure 5:
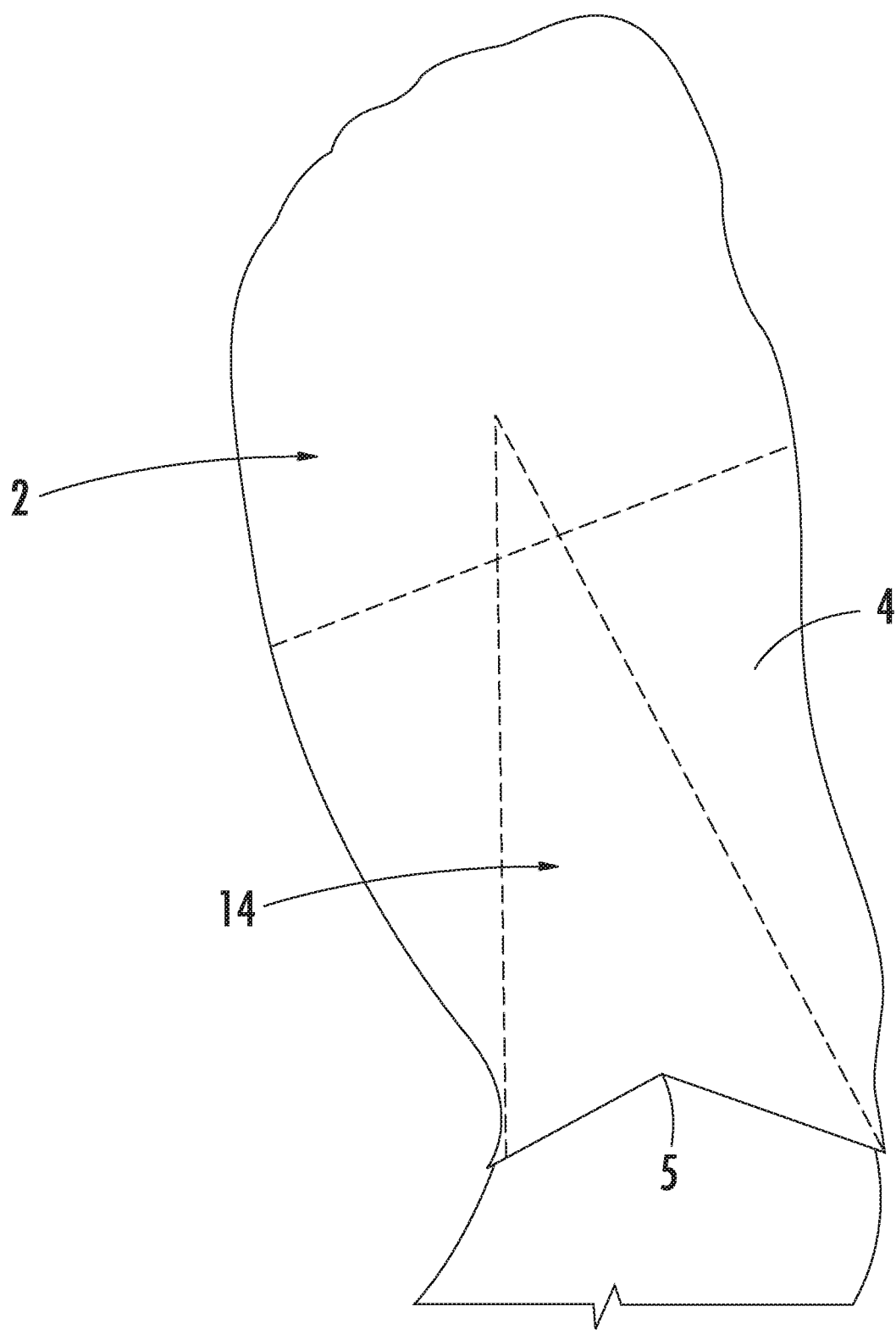
FIG. 5 illustrates a top schematic view of a sock according to another implementation.

In addition, a dorsal surface portion of the midfoot portion 4 of sock 10 may define a slight "V" shaped cut out 5 adjacent leg opening 8 defined by the ankle portion 1, such as is shown in FIGS. 4 and 5.

The forefoot portion 2 includes a dorsal surface portion 3 and a plantar surface portion 21 and defines a pocket in which the wearer's toes and forefoot may extend. The plantar surface portion 21 is configured for being disposed below the plantar surface of the wearer's foot when worn, and the dorsal surface portion 3 is configured for being disposed above the wearer's foot.

The length of the forefoot portion 2 of sock 10 as measured between a proximal end abutting the midfoot portion 4 and a distal end of the forefoot portion 2 tapers downwardly from an inner (or medial) side of the sock 10 to an outer (or lateral) side of the sock 10. The inner side of the sock 10 is configured to fit adjacent an inner (or medial) side of the wearer's foot, and an outer side of the sock 10 is configured to fit adjacent an outer (or lateral) side of the wearer's foot. This tapering provides a closer fit of the forefoot portion 2 against the wearer's toes. In such an implementation, the sock 10 for the right foot tapers in one direction and the sock of the left foot tapers in the other direction.

In other implementations (not shown), the forefoot portion 2 may define two or more toe pockets that are each configured for receiving one or more toes of the wearer. For example, the forefoot portion 2 may include five pockets that are each configured for receiving one toe of the wearer. In another example, the forefoot portion 2 may include a first pocket for receiving a big toe of the wearer and a second pocket for receiving the remaining toes. The pockets may be integrally knit with the other portions of the sock. For example, in one implementation, the pockets may be joined together and to the rest of the sock by a seamless knit. These toe pockets may assist in providing a more barefoot feel to the wearer.

Further, in some implementations (not shown), a central portion of the midfoot portion 4 between the high compression bands 40, 41 may include a mesh-style knit pattern to provide ventilation below an arch portion of the wearer's foot. The mesh-style knit pattern may also be provided on the dorsal portion of the midfoot portion in addition to or instead of the mesh-style knit pattern on the plantar portion of the midfoot portion, according to other implementations. For example, as shown in FIG. 5, the upper mesh-style knit pattern 14 may be substantially V or U-shaped, with the apex adjacent the forefoot portion 2 or adjacent a distal end of the midfoot portion 4.

The plantar surface portion 21 may include a shock absorbent element to provide shock absorbency (or dissipation) to the wearer's forefoot. The shock absorbent element may include a sock absorbing yarn knit or laid in to the plantar surface portion 21 or a shock absorbent material coupled to the plantar surface portion 21. For example, in the implementation shown in FIG. 3, the shock absorbent element includes a 3 end, polyester, air textured yarn around Spandex yarn that is woven into the plantar surface portion 21. In other implementations, other types of air textured yarns, silicone yarns (e.g., low grade), or other suitable shock absorbing yarns may be used. In addition, the plantar surface portion 21 may extend at least partially around the sides of the foot.

In addition, in some implementations, the plantar surface portion 21 includes a traction element to provide proper traction for the wearer when moving across surfaces. The traction element may include a layer of adhesive (or glue), silicone yarn woven into the plantar surface portion 21, another suitable type of yarn that can be woven into the plantar surface portion 21 and provide adequate traction for the wearer, one or more foam pads adhered or otherwise coupled to the plantar surface portion 21, and/or other suitable material coupled to the plantar surface portion 21.

In some implementations, the plantar surface portion 21 of the forefoot portion 2 may include a silicone yarn (or thread) knit into the plantar surface portion 21 to provide traction and shock absorption. In other implementations, silicone or other suitable material may be heat pressed onto the plantar surface portion of the sock 10 to provide traction and shock absorption. The traction may be relatively high to mimic the feel of dancing barefoot on all floor surfaces. Furthermore, in certain implementations, the material providing traction may be durable (e.g., last 6 months or more), comfortable, allow for the wearer to turn and jump, and thin so as to avoid interrupting the movement of the wearer.

In other implementations (not shown), at least a portion of the forefoot portion 2 may include a honeycomb knit pattern to mimic natural foot skin. This honeycomb knit pattern may provide better traction and shock absorbency.

FIGS. 6A through 6F illustrate a sock 100 according to another implementation that includes a distal high compression zone, or area, 141 that extends from the intermediate arch band 142 to the proximal edge of the forefoot portion 102 and a proximal high compression zone 140 that extends from a heel opening 106 to the intermediate arch band 142. The zones 140, 141 and intermediate arch band 142 extend around the circumference of the sock 100. Similarly to the implementation described above in relation to FIGS. 1 through 3, the intermediate arch band 142 provides less compression to the wearer's foot than the compression zones 140, 141 adjacent to the arch band 142. This reduced compression band 142 may allow for improved circulation through the wearer's foot. The intermediate arch band 142 may include a different knit structure and/or a less dense knit structure than the high compression zones 140, 141, according to some implementations.

The intermediate arch band 142 disposed between the high compression zones 140, 141 provides less compression than the zones 140, 141. For example, the ideal average compressive strength to be applied by the high compression zones 140, 141 may be at least about 24 mmHg (e.g., between about 24 mmHg and about 30 mmHg), and the ideal average compressive strength to be applied by the intermediate arch band 142 may be greater than 75% (e.g., greater than 75%, greater than 80%, greater than 85%, greater than 90%, or greater than 95%) of the average compressive strength applied by the high compression zones 140, 141. For example, the ideal average compressive strength of the high compression zones 140, 141 may be between about 24 mmHg and about 25 mmHg, and the ideal average compressive strength of the intermediate arch band 142 may be between about 19 mmHg and about 20 mmHg. As another example, the ideal average compressive strength of high compression zone 140 may be between about 25 and about 26 mmHg, the ideal average compressive strength of high compression zone 141 may be between about 26 and 27 mmHg, and the ideal average compressive strength of the intermediate arch band 142 may be between about 21 mmHg and about 23 mmHg.

Because the high compression zones 140, 141 and intermediate arch band 142 of sock 100 do not have an axial length greater than a minimum axial length required for known compression testing equipment and methods, the average compressive strength for each zone 140, 141 and band 142 may be estimated by testing one or more samples of a knit tube that is formed using the same specifications as are used to form the respective zone 140, 141 and band 142 and is knit to be at least the minimum axial length required for testing. The sample knit tube(s) may have a circumference of 23 mm and be tested using a modified BS 6612 test method on a CMD-100 Compression Measurement Test System.

The ankle portion 101 of the sock 100 includes a single band that extends around the wearer's lower leg above the heel opening 106 and is disposed below the distal end of the lateral malleolus when worn. The ankle portion 101 includes two bands that each have a proximal end that is continuously knit with (and includes the same knit pattern and density as) the proximal high compression zone 140. Each band also has a distal end, and the distal ends are coupled together along a seam. The ankle portion 101 provides the same or a similar level of compression as the proximal high compression zone 140, for example.

In addition, a seam may join a portion of a distal edge of the plantar surface portion 121 and a distal edge of the dorsal surface portion of the forefoot portion 102. And, in some implementations, the plantar surface portion 121 may be configured to have little or no compression on the wearer's foot (e.g., less than 15 mmHg). Furthermore, one or more traction elements 122 may be disposed adjacent at least a portion of the plantar surface portion 121 of sock 100 in FIG. 6B. The traction elements 122 may include any of the options listed above in relation to FIG. 3, for example.

Figure 6B:
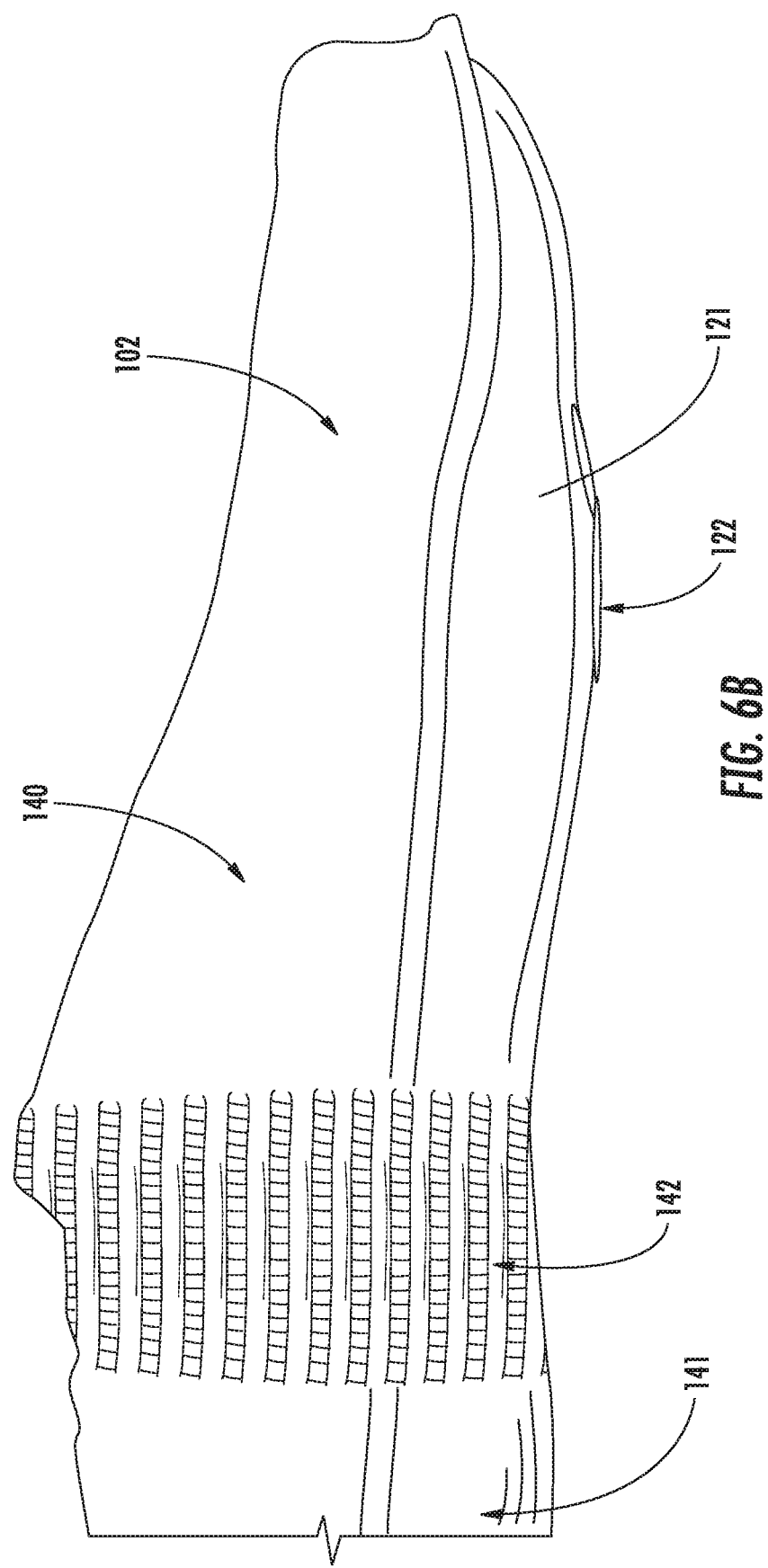
FIG. 6B illustrates a partial view of an inner side of the sock of FIG. 6A.
Figure 6C:
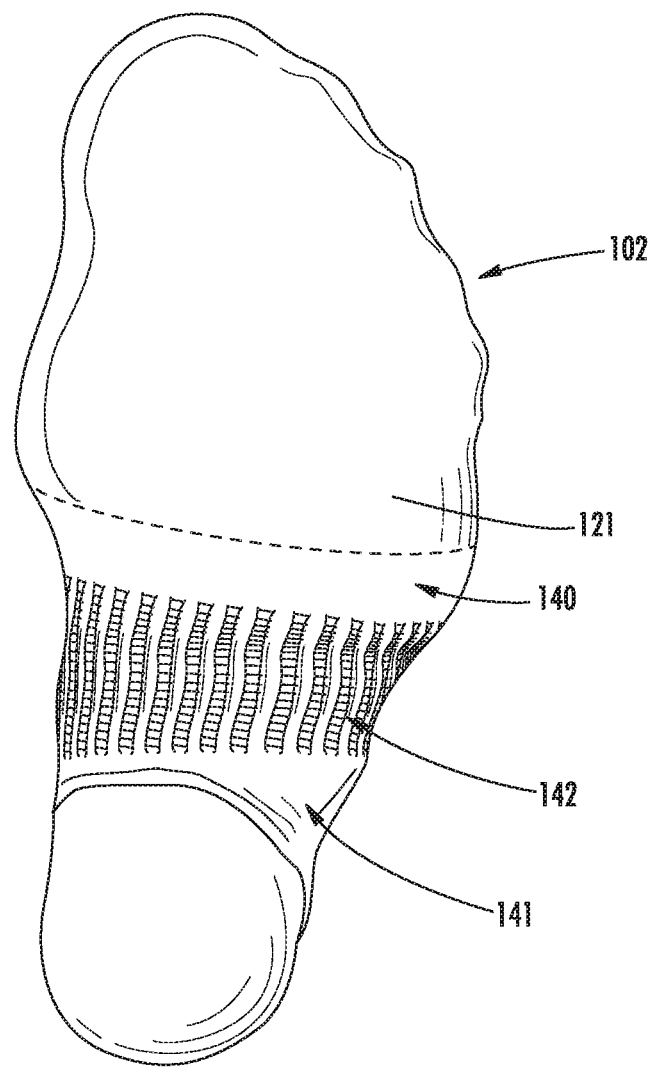
FIG. 6C illustrates a bottom view of the sock of FIG. 6A.
Figure 6F:
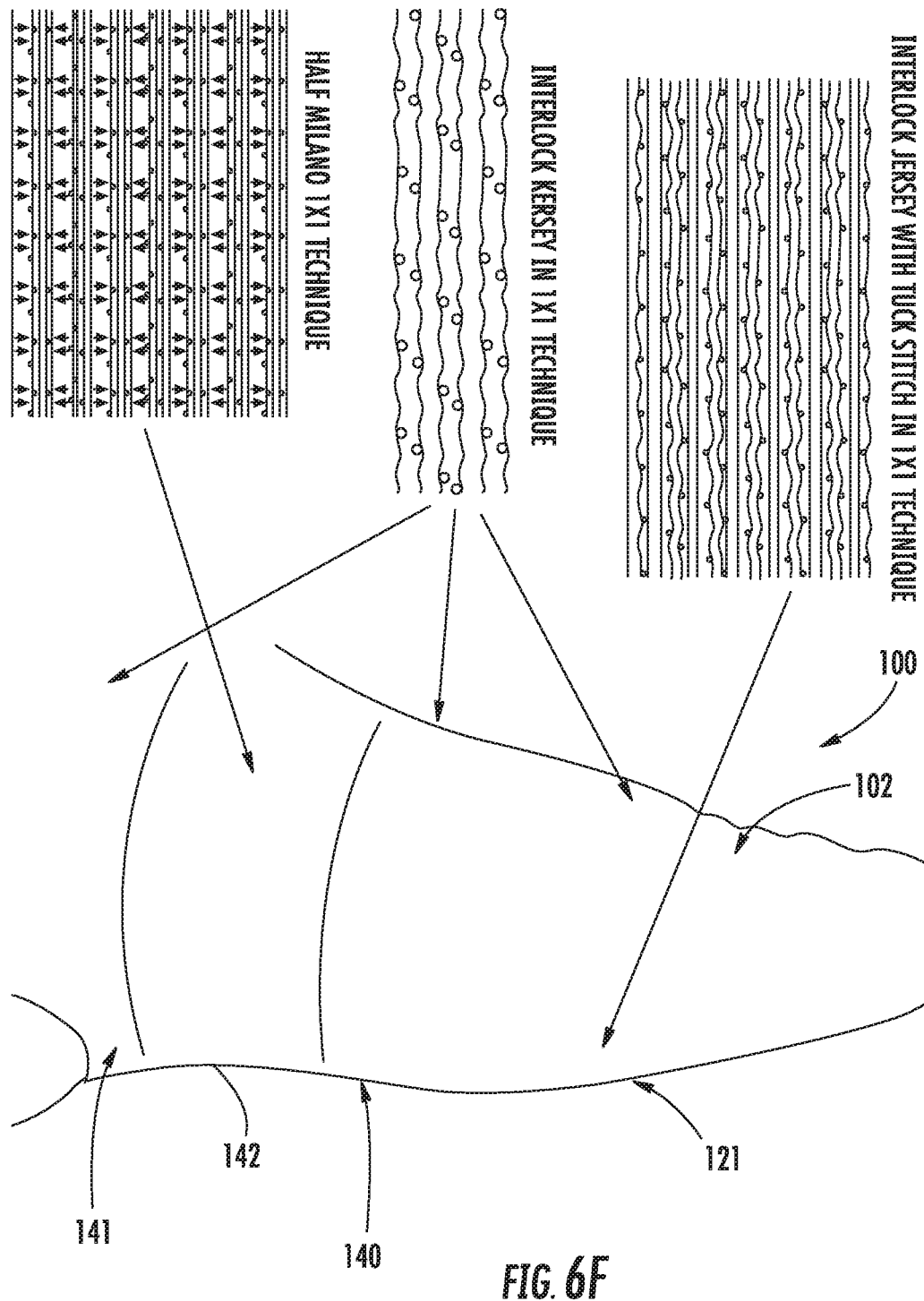
FIG. 6F illustrates a partial view of the inner side of the sock of FIG. 6A.

As shown in FIG. 6F, high compression zones 140, 141 and the dorsal portion of the forefoot portion 102 of the sock 100 are formed using an interlock jersey stitch in 1×1 technique. In this implementation, the dorsal portion of the forefoot portion 102 and the distal high compression zone 141 may include the same or similar level of compressive strength. Ankle portion 101 may also be formed using this stitch and may include the same or similar level of compressive strength as the proximal high compression zone 140. The plantar portion 121 of the forefoot portion 102 is formed using an interlock jersey with a tuck stitch in 1×1 technique. And, the intermediate arch band 142 is formed using a half Milano stitch in 1×1 technique. Other suitable stitches and techniques may be used for these various areas of the sock 100 according to other implementations.

The sock 100 may or may not include the crescent shaped mesh knit portion 130 on the ankle portion 101 shown in FIG. 6A, according to certain implementations.

Figure 7:
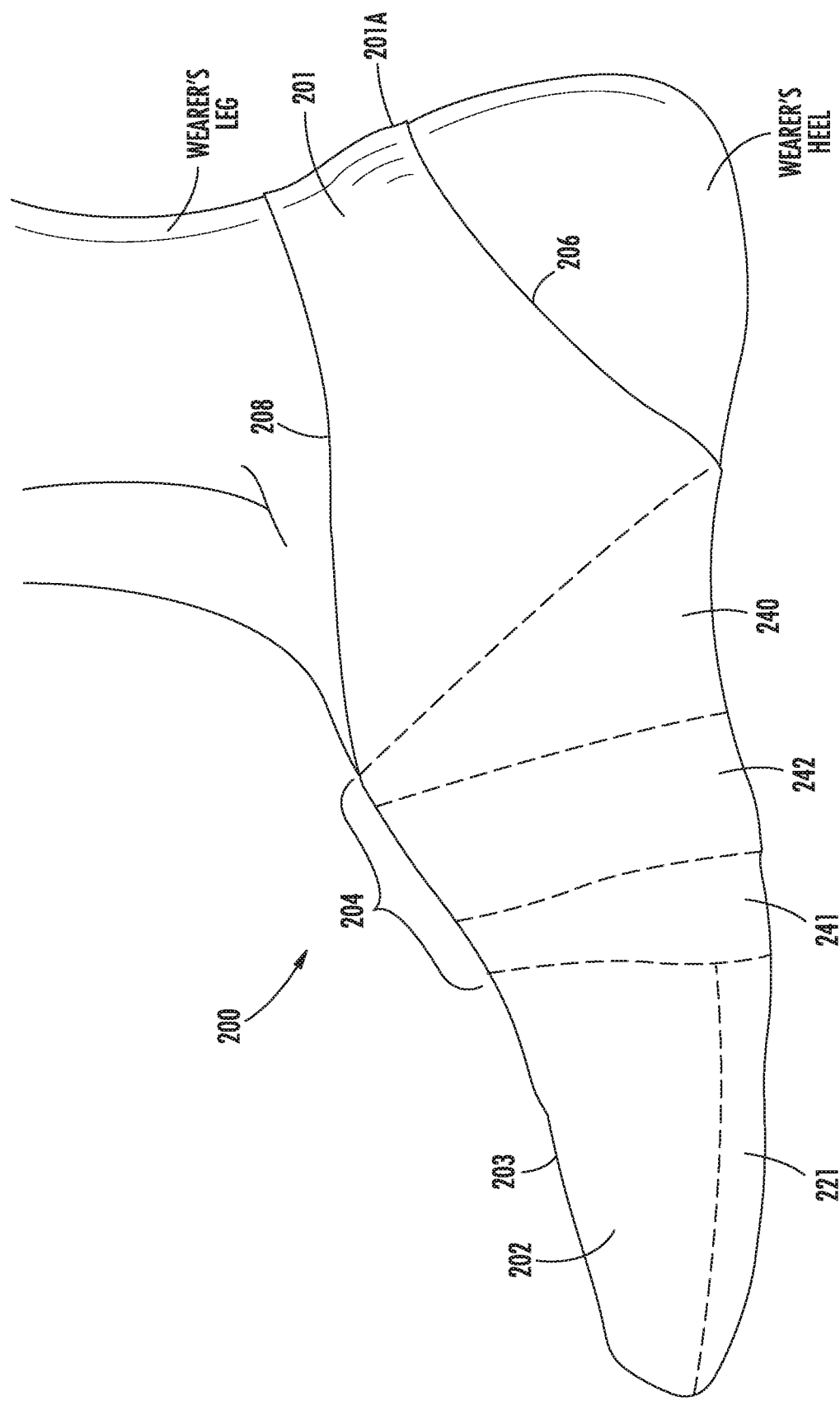
FIG. 7 illustrates an inner side view of a sock according to another implementation.
Figure 8:
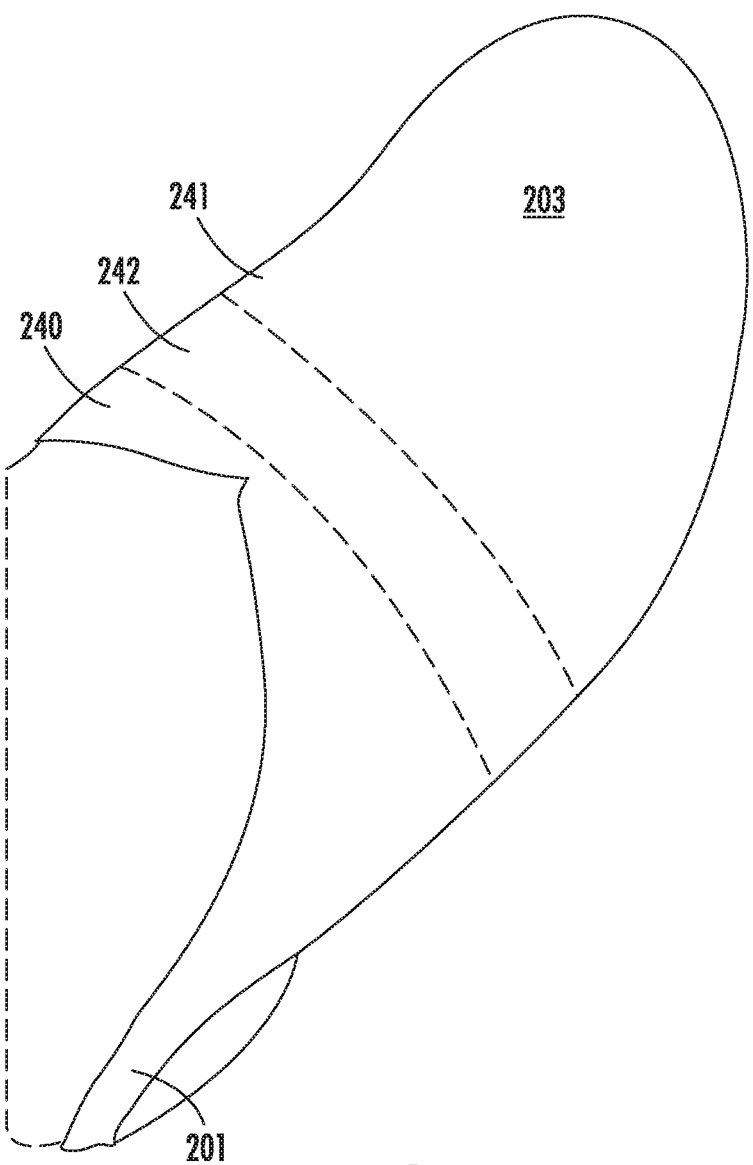
FIG. 8 illustrates a partial top view of the sock of FIG. 7.

FIGS. 7 and 8 illustrate another implementation of a sock 200. The sock 200 may be knit on a flat knitting machine. The seam at the forefoot portion 202 may be machine sewn during the knitting of the sock 200, and the seam coupling distal ends of the ankle bands 201a may be sewn after knitting is completed.

In addition, a dorsal surface portion of the midfoot portion 204 of sock 200 defines a slight "V" shaped cut out 205 adjacent leg opening 208 defined by ankle portion 201.

The ankle bands of the ankle portion 201 are knit together and with the same or similar level of compression as the first high compression zone 241. The distal ends of the ankle bands are coupled together via a seam, as described above in relation to FIGS. 6A-6F. Similarly, the forefoot portion 201 is knit together with the second high compression zone 240. The dorsal surface portion 203 of the forefoot portion 201 provides the same or similar level of compression as the second high compression zone 240, and the plantar surface portion 221 of the forefoot portion 201 is configured to provide little or no compression. For example, the plantar surface portion 221 may be configured for providing about 15 mmHg or less of compression.

A reduced compression zone 242 is disposed between and knit together with the high compression zones 241, 240. The reduced compression zone 242 provides less compression than the high compression zones 241, 240. The high compression zones 240, 241 and reduced compression zone 242 extend around the circumference of the midfoot portion 204 360°.

For example, the ideal average compressive strength to be applied by the high compression zone 240, 241 may be at least about 24 mmHg (e.g., between about 24 mmHg and about 30 mmHg), and the ideal average compressive strength to be applied by the reduced compression zone 242 may be greater than 75% (e.g., greater than 75%, greater than 80%, greater than 85%, greater than 90%, or greater than 95%) of the average compressive strength applied by the high compression zones 240, 241. For example, the ideal average compressive strength of the high compression zones 240, 241 may be between about 24 mmHg and about 25 mmHg, and the ideal average compressive strength of the reduced compression zone 242 may be between about 19 mmHg and about 20 mmHg. As another example, the ideal average compressive strength of high compression zone 240 may be between about 25 and about 26 mmHg, the ideal average compressive strength of high compression zone 241 may be between about 26 and 27 mmHg, and the ideal average compressive strength of the reduced compression zone 242 may be between about 21 mmHg and about 23 mmHg.

Because the various zones 240, 241, 242 of sock 200 do not have an axial length greater than a minimum axial length required for known compression testing equipment and methods, the average compressive strength for each zone 240, 241, 242 may be estimated by testing one or more samples of a knit tube that is formed using the same specifications as are used to form the respective zone 240, 241, 242 and is knit to be at least the minimum axial length required for testing. The sample knit tube(s) may have a circumference of about 27.33 mm and be tested using a modified BS 6612 test method on a CMD-100 Compression Measurement Test System.

The plantar surface portion 221 of the forefoot portion 202 includes a shock absorbing yarn for providing shock absorbency to the wearer. For example, the shock absorbing yarn may include a 4/100/34 Nylon yarn that can dissipate some of the shock incident on the sock 200 during exercise or movement.

In addition, a layer or film of hot adhesive (glue) may be applied, such as with a roller, onto an external plantar surface portion 221 of the forefoot portion 201 and allowed to dry. The layer of dried adhesive provides additional traction for the sock 200. For example, the coefficient of friction of the sock 200 with the layer of adhesive is higher than the coefficient of friction of the sock 200 without the adhesive layer. In other implementations (not shown), the adhesive may be applied in discrete, spaced apart areas or over a portion of the plantar surface portion 221 (e.g., dots, stripes, a grid, or other suitable patterns). In addition, in some implementations, at least a portion of the adhesive layer may be covered with a layer of paint.

In other implementations (not shown), one or both of compression bands or zones may be disposed at other locations along the midfoot portion, depending on where a higher compressive structure may be useful. In addition, other implementations (not shown) may include more than two compression bands or zones or just one compression band or zone.

In addition, in certain implementations, the size of the opening for the heel may be reduced to provide additional support for the sides of the ankle of the wearer and/or to anchor the proximal high compression band or zone closer to the point at which the plantar fascia meets the calcaneus. In addition, in other implementations, a compressive zone may be provided on a lateral and/or medial side of the ankle portion to provide additional support for the ankle.

The implementations of the socks shown in FIGS. 1 through 8, respectively, may be manufactured on a flat knitting machine. However, other machines and manufacturing methods may be used to manufacture the sock or other implementations thereof.

In addition, the following types of yarn are knit in sock 10: 150 denier with 96 filament, wherein the white yarn shown is 3 ends of polyester spandex, and the black yarn shown is 2 ends of spandex (e.g., LYCRA) covered in polyester. However, other specifications may be selected for the various types of yarn used for the sock 10 depending on the intended locations of more or less compression relative to the wearer's foot and the need for shock absorbency. For example, in socks 100, 200 shown in FIGS. 6A through 8, 140 Spandex DC 1/70/34 wicking textured nylon yarn may be used to knit the compressive bands 140, 141, arch band 142, and the ankle portion 101, and 140 Spandex DC 4/100/34 textured nylon may be used to knit the plantar surface portion 121 of the sock 100.

The yarns selected may also have or be treated to have antimicrobial and/or moisture wicking properties.

The sock may include one or more colors of yarn. For example, the sock 10 shown in FIG. 1 includes three colors, and the socks 100, 200 shown in FIGS. 6A-6F and 7-8, respectively, have one color. The socks may be black or nude toned, for example.

And, in some implementations, the sock may also be manufactured to provide various options, such as various sizes to accommodate various foot sizes, various compression levels to accommodate various preferences for arch (or plantar fascia) support, and/or various colors or patterns.

Figure 9:
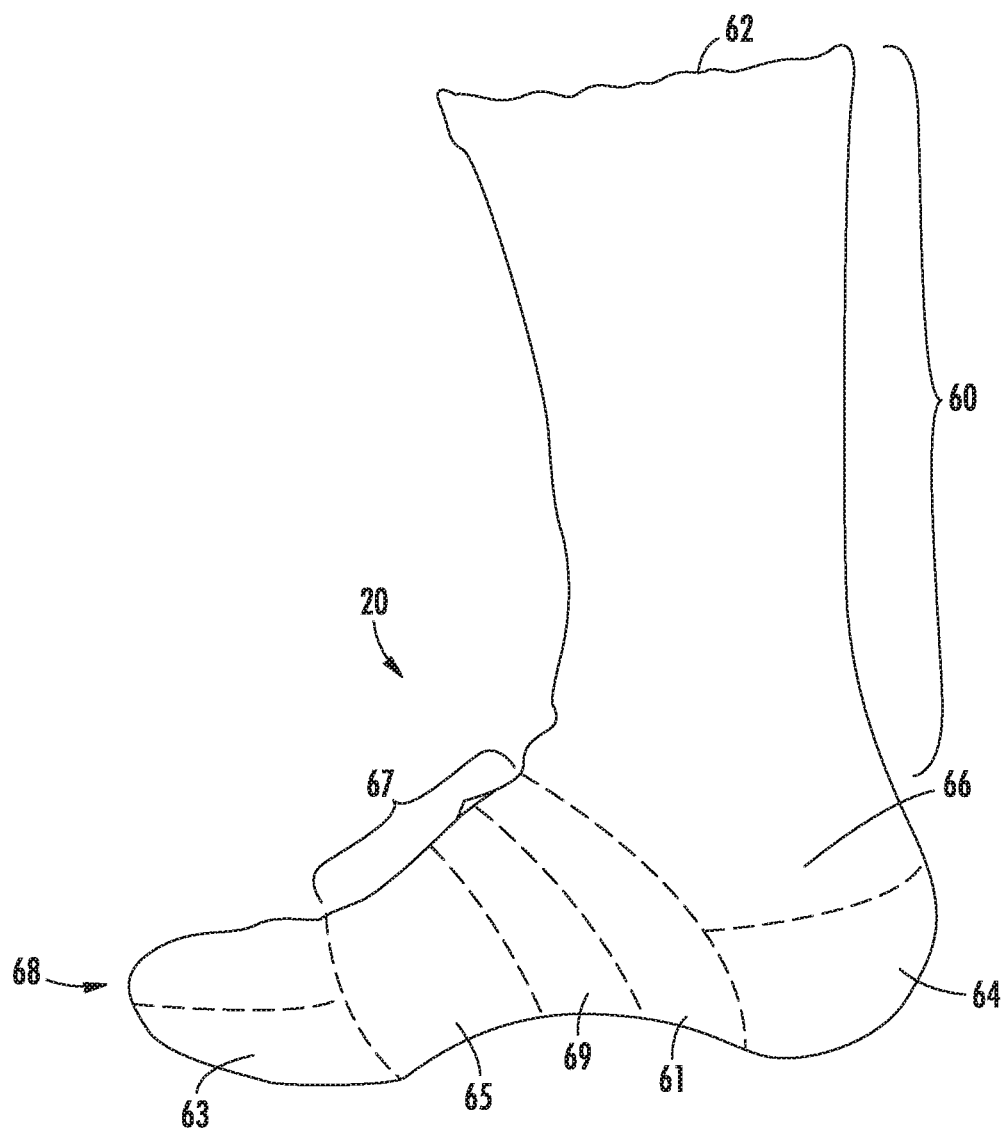
FIG. 9 illustrates a side view of a sock according to another implementation.

Another implementation of the sock is shown in FIG. 9. This sock 20 does not include the heel opening and includes a leg portion 60 that is configured to extend up the wearer's leg from an ankle portion 66. The ankle portion 66 extends below and around the lateral malleolus and medial malleolus to support the ankle. The sock 20 also includes a heel portion 64 below the ankle portion 66 that is configured for extending below and behind the calcaneus when worn. The heel portion 64 provides less compressive strength than the ankle portion 66. For example, the heel portion 64 may provide a similar amount of compressive strength as the plantar surface portion 63 of the forefoot portion 68, and in some implementations, the amount of compression is relative low or substantially zero, depending on the width or size of the wearer's foot.

In addition, the heel portion 64 may have one or more traction elements coupled to the plantar exterior surface of the heel portion 64 and/or shock absorbing elements similar to the plantar surface portion 63 of the forefoot portion 68.

In one implementation, the leg portion 60 provides graduated compression that increases from the ankle portion 66 toward a leg opening 62 defined at a distal end of the leg portion 60. For example, the average compressive strength adjacent the ankle portion 66 may be at least about 24 mmHg (e.g., around 25 mmHg), and the average compressive strength decreases gradually toward the leg opening 62 to at least about 15 mmHg (e.g, about 17 to about 18 mmHg). And, the average compressive strength of the ankle portion 66 may be the same as, less than, or higher than the average compressive strength of a first high compression zone 61 extending around the midfoot portion 67 adjacent the ankle portion 66. In addition, a second high compression zone 65 extending around the midfoot portion 67 adjacent the forefoot portion 68 may have the same, higher, or lower average compressive strength as the first high compression zone 61 and/or the ankle portion 66. Similar to the implementations described above, the midfoot portion 67 also includes a reduced compression zone 69 extending around the midfoot portion 67 and disposed between the first high compression zone 65 and the second high compression zone 65. The reduced compression zone 69 has an average compressive strength that is less than the average compressive strength of the first compression zone 61 and the second compression zone 65. And, in some implementations, the reduced compression zone 69 has an average compressive strength that is less than the average compressive strength of the ankle portion 66.

For example, the ideal average compressive strength to be applied by the high compression zones 65, 61 may be at least about 24 mmHg (e.g., between about 24 mmHg and about 30 mmHg), and the ideal average compressive strength to be applied by the reduced compression zone 69 may be greater than 75% (e.g., greater than 75%, greater than 80%, greater than 85%, greater than 90%, or greater than 95%) of the average compressive strength applied by the high compression zones 65, 61. For example, the ideal average compressive strength of the high compression zones 61, 65 may be between about 24 mmHg and about 25 mmHg, and the ideal average compressive strength of the reduced compression zone 69 may be between about 19 mmHg and about 20 mmHg. As another example, the ideal average compressive strength of high compression zone 65 may be between about 25 and about 26 mmHg, the ideal average compressive strength of high compression zone 61 may be between about 26 and 27 mmHg, and the ideal average compressive strength of the reduced compression zone 69 may be between about 21 and 23 mmHg.

Because the various zones 61, 65, 69 of sock 20 do not have an axial length greater than a minimum axial length required for known compression testing equipment and methods, the average compressive strength for each zone 61, 65, 69 may be estimated by testing one or more samples of a knit tube that is formed using the same specifications as are used to form the respective zone 61, 65, 69 and is knit to be at least the minimum axial length required for testing. The sample knit tube(s) may have a circumference of about 23 mm and be tested using a modified BS 6612 test method on a CMD-100 Compression Measurement Test System.

In another implementation, the leg portion 60 does not provide graduated compression.

In some implementations, the sock 20 may also be manufactured to provide various options, such as various sizes to accommodate various foot, ankle, and/or calf sizes, various compression levels to accommodate various preferences for arch (or plantar fascia) support, and/or various colors or patterns.

According to various implementations, sock 20 includes the following yarns: a 20 denier Spandex air covered yarn with 1/150/68 Amy Sorbtek yarn for a body plating of the entire sock, a double covered 420 denier Spandex DC 1/70/34 Nylon yarn laid in for the leg portion 60 and foot portions 67, 68, a 3/70/34 and 2/70/34 Nylon yarn knit in for the heel portion 64 and the plantar surface portion 63, and a 4/70/34 Nylon yarn knit in for the body of the sock 20. The 2/70/34 yarn and 3/70/34 yarn are high spliced to the surface of the 4/70/34 yarn for additional padding in the plantar surface area 63 and the heel portion 64. However, in other implementations, other yarns may be used in other configurations to provide alternative levels of compression and/or shock absorbency.

In addition, various stitching techniques may be used to form the sock 20. For example, a double welt around the leg opening 62 and the body may be formed using a 1×1 mock rib technique. The plantar surface area 63 and heel portion 64 may formed using a terry stitch, with a half cushion construction around the plantar surface area 63 and full cushion ring toe construction.

Figure 10:
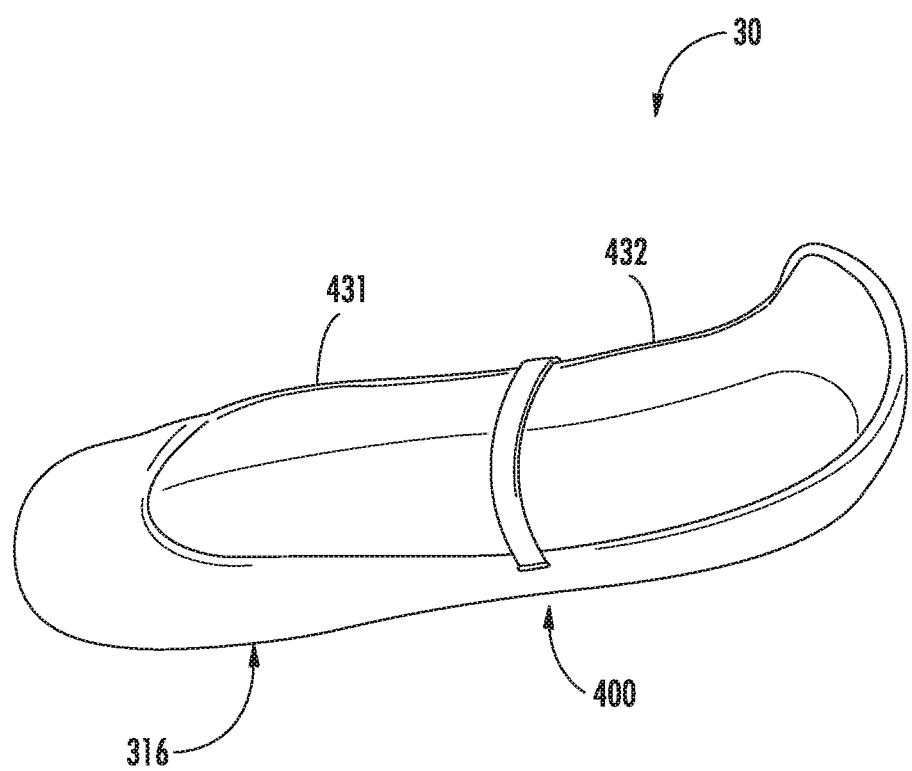
FIG. 10 illustrates a perspective view of a sock according to yet another implementation.

Yet another implementation of the sock 30 is shown in FIG. 10. This sock may be useful for ballet dancers because it looks like a ballet shoe but provides the ankle, arch, and compressive support provided by socks 10, 20, 100, 200 described above. The sock 30 may serve as the ballet shoe or may be worn between the wearer's foot and the ballet shoe. For implementations in which the sock 30 is worn without a ballet shoe, a traction element is included on the plantar surface portion 316 of the forefoot portion. This traction element may be more than, less than, or the same as the traction described above for socks 10, 20, 100, 200. For example, sock 30 may have a medium level of traction suitable for use with marley or wood floor surfaces expected by ballet dancers. In addition, the traction element may be rolled or heat pressed onto the plantar surface of the forefoot portion, integrally knit into the forefoot portion, or otherwise externally coupled to the plantar surface portion 316. In addition, the sock 30 defines one or more openings 430, 431 configured to be adjacent a dorsal surface portion of the midfoot portion 400 that is above the arch of the wearer's foot, similar to a traditional ballet shoe. The sock 30 may be knit from one or more yarns or formed from other materials, such as leather, faux leather (e.g., vinyl), or fabric.

In some implementations, the sock 30 may also be manufactured to provide various options, such as various sizes to accommodate various foot sizes and/or various compression levels to accommodate various preferences for arch (or plantar fascia) support. Although the color of the sock 30 is typically a traditional shade of pink or other color used for ballet shoes, other colors and/or patterns not traditionally used with ballet shoes may be used.

The socks 10, 20, 30, 100, 200 may be packaged in small mesh bags, which provide ventilation and provide a storage solution for the wearer when the socks are not being worn. The mesh bag can be washed as well.

Furthermore, certain implementations may include insignia that may be embroidered or heat pressed onto the sock. Other suitable attachment mechanisms may be used as well.

In addition, in certain implementations, information indicating how to care for the socks may be included on the sock by heat pressing or other suitable mechanism.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

The invention claimed is:

1. A wearable foot garment comprising: a forefoot portion having a plantar area and a dorsal area; a midfoot portion having a proximal edge; and an ankle portion comprising an ankle band, the ankle band having a first edge that defines a leg opening and a second edge that defines a heel opening with the proximal edge of the midfoot portion, the leg opening being configured for receiving a leg of the wearer; and the heel opening configured for receiving at least a portion of a heel of the wearer,
wherein:
the plantar area of the forefoot portion comprises an adhesive film disposed on an external surface of the plantar area, the adhesive film having a co-efficient of friction that is higher than an external surface of the midfoot portion, wherein at least a portion of the adhesive film is configured for engaging a ground surface when the wearable foot garment is worn by the wearer;
wherein: the midfoot portion comprises a, first high compression zone, a second high compression zone, and a reduced compression zone disposed between the first and second high compression zones;
the first high compression zone and the second high compression zone extend at least along a plantar area of the midfoot portion and at least partially around a circumference of the midfoot portion,
the first high compression zone is configured for providing compression in a radially inward direction toward the wearer's foot adjacent a proximal end of the wearer's plantar aponeurosis,
the second high compression zone is configured for providing compression in a radially inward direction toward the wearer's foot adjacent distal ends of metatarsals of the wearer,
the reduced compression zone extends at least along the plantar area of the midfoot portion and at least partially around the circumference of the midfoot portion, the reduced compression zone is disposed between the first and second high compression zones, and
a first compressive strength in the first high compression zone and a second compressive strength associated in the second compression zone are greater than a third compressive strength in the reduced compression zone.

2. The wearable foot garment of claim 1, wherein the plantar area of the forefoot portion comprises a shock absorbing yarn.

3. The wearable foot garment of claim 1, wherein the ankle band comprises a first ankle band portion and a second ankle band portion, each of the first and second ankle band portions comprises a proximal end knit together with the midfoot portion adjacent the first high compression zone and a distal end, the distal ends are coupled together along a seam.

4. The wearable foot garment of claim 3, wherein the proximal ends of the ankle bands, the midfoot portion, and the forefoot portion are knit together seamlessly.

5. The wearable foot garment of claim 1, wherein the ankle band has a compressive strength that is substantially the same as the compressive strength of the first high compression zone.

6. The wearable foot garment of claim 1, wherein the dorsal area of the forefoot portion has substantially the same compressive strength as the first high compression zone, and the plantar area of the forefoot portion has less compressive strength than the first high compression zone.

7. The wearable foot garment of claim 1, wherein the first high compressive zone, the second high compressive zone, and/or the reduced compression zone extend around the circumference of the midfoot portion 3600.

8. The wearable foot garment of claim 1, wherein the first and second high compression zones and the reduced compression zone are knit together seamlessly.

9. A wearable foot garment comprising:
a midfoot portion having a proximal edge; and
an ankle portion comprising an ankle band, the ankle band having a first edge that defines a leg opening and a second edge that defines a heel opening with the proximal edge of the midfoot portion, the leg opening being configured for receiving a leg of the wearer, and the heel opening configured for receiving at least a portion of a heel of the wearer, wherein:
the midfoot portion comprises a first high compression zone, a second high compression zone, and a reduced compression zone disposed between the first and second high compression zones;
the first high compression zone and the second high compression zone extend at least along a plantar area of the midfoot portion and at least partially around a circumference of the midfoot portion,
the first high compression zone is configured for providing compression in a radially inward direction toward the wearer's foot adjacent a proximal end of the wearer's plantar aponeurosis,
the second high compression zone is configured for providing compression in a radially inward direction toward the wearer's foot adjacent distal ends of metatarsals of the wearer,
the reduced compression zone extends at least along the plantar area of the midfoot portion and at least partially around the circumference of the midfoot portion, the reduced compression zone is disposed between the first and second high compression zones, and
a first compressive strength in the first high compression zone and a second compressive strength associated in the second compression zone are greater than a third compressive strength in the reduced compression zone.

10. The wearable foot garment of claim 9, wherein the ankle band comprises a first ankle band portion and a second ankle band portion, each of the first and second ankle band portions comprises a proximal end knit together with the midfoot portion adjacent the first high compression zone and a distal end, the distal ends are coupled together along a seam.

11. The wearable foot garment of claim 10, wherein the proximal ends of the ankle bands and the midfoot portion are knit together seamlessly.

12. The wearable foot garment of claim 9, wherein the ankle band has a compressive strength that is substantially the same as the compressive strength of the first high compression zone.

13. The wearable foot garment of claim 9, wherein the first high compressive zone, the second high compressive zone, and/or the reduced compression zone extend around the circumference of the midfoot portion 360°.

14. The wearable foot garment of claim 9, wherein the first and second high compression zones and the reduced compression zone are knit together seamlessly.

* * * * *